United States Patent
Black

(10) Patent No.: US 9,645,049 B2
(45) Date of Patent: May 9, 2017

(54) SOOT GENERATING DEVICE

(71) Applicant: ROLLS-ROYCE PLC, London (GB)

(72) Inventor: John David Black, Dunoon (GB)

(73) Assignee: ROLLS-ROYCE plc, London (GB)

( * ) Notice: Subject to any disclaimer, the term of this patent is extended or adjusted under 35 U.S.C. 154(b) by 497 days.

(21) Appl. No.: 14/470,254

(22) Filed: Aug. 27, 2014

(65) Prior Publication Data

US 2015/0076331 A1    Mar. 19, 2015

(30) Foreign Application Priority Data

Sep. 19, 2013  (GB) .................................. 1316637.6

(51) Int. Cl.
| | | |
|---|---|---|
| *G01M 15/10* | (2006.01) | |
| *G01N 21/71* | (2006.01) | |
| *G01N 5/00* | (2006.01) | |
| G01N 15/00 | (2006.01) | |
| G01N 15/06 | (2006.01) | |

(52) U.S. Cl.
CPC ............ *G01M 15/108* (2013.01); *G01N 5/00* (2013.01); *G01N 21/71* (2013.01); *G01N 15/0606* (2013.01); *G01N 2015/0046* (2013.01); *G01N 2201/06113* (2013.01); *G01N 2201/127* (2013.01)

(58) Field of Classification Search
CPC ............ G01M 15/108; G01N 15/0606; G01N 2015/0046; G01N 21/71; G01N 2201/06113; G01N 2201/127; G01N 5/00
See application file for complete search history.

(56) References Cited

U.S. PATENT DOCUMENTS

| | | | | |
|---|---|---|---|---|
| 5,051,090 A | * | 9/1991 | Anzawa | .................... F23D 5/00 |
| | | | | 431/211 |
| 5,206,176 A | * | 4/1993 | Beer | ................... G01N 21/6402 |
| | | | | 110/185 |
| 6,946,101 B1 | | 9/2005 | Jing | |
| 7,167,240 B2 | * | 1/2007 | Stagg | ..................... B82Y 30/00 |
| | | | | 356/337 |
| 8,287,825 B1 | * | 10/2012 | Namazian | ................. C01B 3/34 |
| | | | | 422/626 |
| 2006/0068350 A1 | * | 3/2006 | Aigner | ................... B82Y 30/00 |
| | | | | 431/326 |

(Continued)

FOREIGN PATENT DOCUMENTS

| | | | | |
|---|---|---|---|---|
| FI | DE 3541215 A1 | * | 5/1987 | .............. F21S 10/02 |
| GB | 208754 A | | 1/1924 | |
| JP | A-57-134604 | | 8/1982 | |

OTHER PUBLICATIONS

Kazuhiro Hayashida and Katsuhiko Haji, Effects of Fuel Properties on Diffusion Combustion and Depost Accumulation, Mar. 14, 2012, InTech, ISBN: 978-953-51-0277-9, www.intechopen.com.*

(Continued)

*Primary Examiner* — Francis Gray
(74) *Attorney, Agent, or Firm* — Oliff PLC

(57) ABSTRACT

A soot generating device suitable for calibration purposes and a method of using the device for calibrating a soot measuring apparatus are presented. The soot generating device includes a wick located relative to a burning zone, a gas diffusion shield surrounding the burning zone that allows a continuous stream of air into the combustion zone, and a fuel supply for delivering fuel to the wick.

13 Claims, 2 Drawing Sheets

(56) References Cited

U.S. PATENT DOCUMENTS

2007/0264172 A1    11/2007  Mosimann et al.
2008/0053195 A1     3/2008  Matter et al.
2015/0064635 A1*    3/2015  Chen .................. F23D 3/08
                                                    431/325

OTHER PUBLICATIONS

Mar. 28, 2014 Search Report issued in British Application No. GB 1316637.6.
Jan. 16, 2015 Search Report issued in European Application No. 14182391.
Smedley, Joanne M., Williams, A. "Soot deposition from ethylene/air flames and the role of aromatic intermediates, ACS Fuels: Symposium on Combustion Chemistry: Large Aromatics, Fullerenes and Soot," (1991) vol. 36, No. 4, pp. 1501-1508.
Hayashida, K., et al. "Effects of Fuel Properties on Diffusion Combustion and Deposit Accumulation, Fossil Fuel and the Environment," (2012) pp. 1-16.

* cited by examiner

SOOT GENERATING DEVICE

TECHNICAL FIELD OF INVENTION

This invention relates to a soot generating device which can produce a known amount of soot.

BACKGROUND OF INVENTION

The examination of pollutants in the exhaust streams of combustion engines is increasingly important area of interest. One key pollutant is soot created during the combustion cycle. There are numerous techniques for measuring the soot, some of which are laser based like the well known laser induced incandescence, LII. However, the equipment used for LII and similar techniques are difficult to calibrate due to the lack of a reliable calibration standard. This invention seeks to provide an improved calibration standard.

STATEMENTS OF INVENTION

In a first aspect, the present invention provides a soot generating device suitable for calibration purposes, comprising: a wick located relative to a burning zone; a gas diffusion shield surrounding the burning zone, the gas diffusion shield allowing a continuous stream of air into the combustion zone; a fuel supply for delivering fuel to the wick; and a collection device for collecting the soot.

The gas diffusion shield may be a gauze material. The gauze material may include apertures having a maximum diameter of less than 2.0 mm.

The wick may be surrounded by a shield. The wick and shield may be coterminous relative to a plane define by the terminal end of the shield The collection device may be a particle filter.

The fuel supply may include an aviation, marine, land transport or other prime mover fuel.

In another aspect, the invention provides a method of calibrating a soot generating device according to the first aspect, comprising: providing the wick with fuel; igniting the fuel so as to provide a flame in the burning zone; burning the fuel for a predetermined time; and, determining a quantity of soot produced for the predetermined time.

The method may further comprise determining the rate of soot production. The quantity of soot may be determined by weighing the deposited amount.

The quantity of soot may be collected in a predetermined time which is in excess of 8 hrs.

In a yet further aspect the invention provides a method of calibrating a laser using the soot generating apparatus according to the first aspect, comprising the steps of: generating a known stream of soot with the soot generator; using a sensor of a soot measuring apparatus to be calibrated to sense the soot stream or a portion thereof; comparing the sensed amount of soot with the known amount of soot to provide a measure of calibration.

The soot measuring apparatus may use a laser induced incandescence technique.

DESCRIPTION OF DRAWINGS

Embodiments of the invention will now be described with the aid of the following drawings of which.

DETAILED DESCRIPTION OF INVENTION

Figure 1:
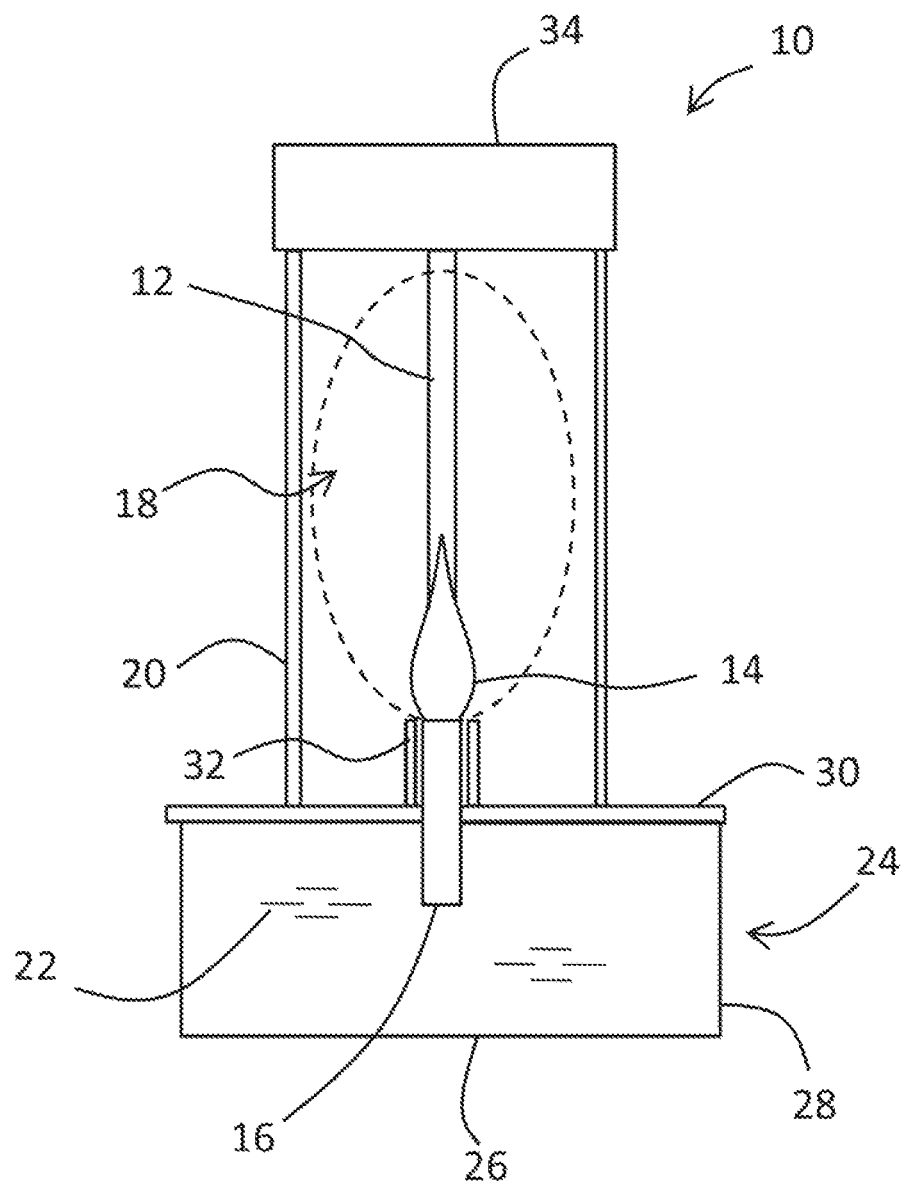
FIG. 1 shows a soot generating device according to the present invention.

FIG. 1 shows a soot generating device 10 according to the present invention. The soot generating device 10 produces a repeatable and constant amount of soot 12 for a given fuel type such that is can be used to calibrate a soot measuring piece of equipment (not shown).

The soot generating device 10 utilises a stable flame 14 to produce soot 12 and includes a wick 16 which is located relative to a burning zone 18 in which the flame 12 sits during normal use. In ordinary use, the wick is located below the burning zone. The burning zone 18 is surrounded by a gas diffusion shield 20 which allows air to pass continuously and evenly into the burning zone 18 for combustion and the production of soot.

The wick 16 receives fuel 22 from a suitable supply, which in the described embodiment, is provided by a small tank 24 located beneath the burning zone 18 and wick 16 when in normal use. The fuel tank 24 includes a vessel having a base 26, on which the soot generating apparatus 10 sits in normal use, side walls 28 and an upper wall 30. The wick 16 passes snugly through the upper wall 30 of the tank 24 with one end located within the fuel 22 so as to allow the fuel 22 to drawn up the wick 16 via capillary action for combustion, as is well known in the art.

A portion of the wick 16 resides above the upper all 30 of the fuel tank 24 and is surrounded by a shield 32. The shield 32 and wick 16 are coterminous such that their respective corresponding ends reside in a common plane at the base of the burning zone 18.

The shield 32 prevents significant amounts of fuel 22 coming out of the side of the wick 16 thereby resulting in a stable supply to be evaporated from the end face of the wick 16. This aids the creation of a stable flame 14. In the present embodiment, the shield 32 is a hollow cylindrical member having an axis along which the wick 16 lies such that the walk of the shield are substantially equidistantly spaced from the wick 16. However, it will be appreciated that other configurations of shield may be possible.

The gas diffusion shield 20 can be any suitable screen or mesh which allows a diffused air flow to enter the burning zone 18 in a uniform and continuous manner to avoid disrupting the stability of the flame 14.

In the present embodiment, the diffusion shield 20 is a gauze structure made from a mesh of interwoven wires. The gauze is provided in a cylindrical configuration so as to provide a substantially even spacing between it and the flame 14 and soot stream 12. Thus, the gas diffusion shield 20 is placed approximately equidistantly from the wick 16 on all sides and is axi-symmetrical with respect to the path of the soot stream 12 when in use in the present embodiment, the gauze is made from wires which have an approximate diameter of 0.3 mm, and which are orthogonally distributed to provide a sheet material having apertures of approximately 1.0 mm. It will be appreciated that a range of wire and aperture dimensions can be considered but it is envisaged that the size of the apertures may range from 0.5 to 2.0 mm, and the wire diameters may range from 0.1 to 0.7 mm.

The soot 12 is gathered by a collection device 34 which is located above the flame 14 and burning zone 18 in normal use. The collection device 34 maybe mounted directly to the gas diffusion shield 20 or may be supported by a frame or other structure which extends up from the tank 24 so as not to disrupt the flow of air entering the burning zone 18. Alternatively, the collection device may be suspended above the gas diffusion shield 20.

The collection device 34 can be any type of suitable particle filter which collects all of the soot particles before exhausting the remaining hot gas to the environment or some form of scrubber (not shown) if required. Examples of suitable collection devices 34 are commercially available quartz filters similar to those used in other soot particle measurement instruments. It will be noted that the filter may also collect unburned hydrocarbon and sulphate, but these can be removed after the collection period by heating the filter to >980° C.

The fuel 22 can be any suitable type, but will preferably be one having a high aromatic content so as to produce a sufficient amount or type of soot 12, or may be specific fuel of interest such as a transport fuel, for example, kerosene.

The fuel tank 24, wick 16, wick shield 32 and gas diffusion shield 20 can be made from materials known in the art which are suitable for the above described purpose. For example, the fuel tank 24 may be plastic or steel, the wick 16 may be cotton or other cellulose fibre or porous ceramic and the wick shield 32 may be a heat tolerant rigid material, such as steel. The gas diffusion shield 20 may be made from a stainless steel.

In use, the soot generating device 10 is placed on a flat and level surface on the base 26 of the fuel tank 24. Fuel 22 is loaded into the fuel tank 24 and allowed to rise up the wick 16. Once the wick 16 is primed, the fuel 22 evaporating from the end of the wick 16 can be lit with an appropriate source of ignition. The gas diffusion shield 20 can then be placed over the flame 14 and left until a steady airflow and flame 14 exists. When the flame 14 and soot 12 have steady flows, the collection device 34 can be added and a timer (not shown) started.

The amount of time which the soot generation is carried out for is dependent on the fuel 22 and the method used to calculate the rate of soot 12 production, but will typically be in excess of 8 hrs. In one embodiment, the soot 12 is collected in a particle filter 34. The particle filter 34 is weighed prior to and after the collection of the soot 12 and the difference measurement used to determine the amount collected. This amount can be then be used with the collection time to determine the rate of soot production. Other quantities may also be calculated such as the density of the soot stream 12. However, this will require an appreciation of the cross sectional area of the stream of soot 12 which can be obtained as described below.

Figure 2:
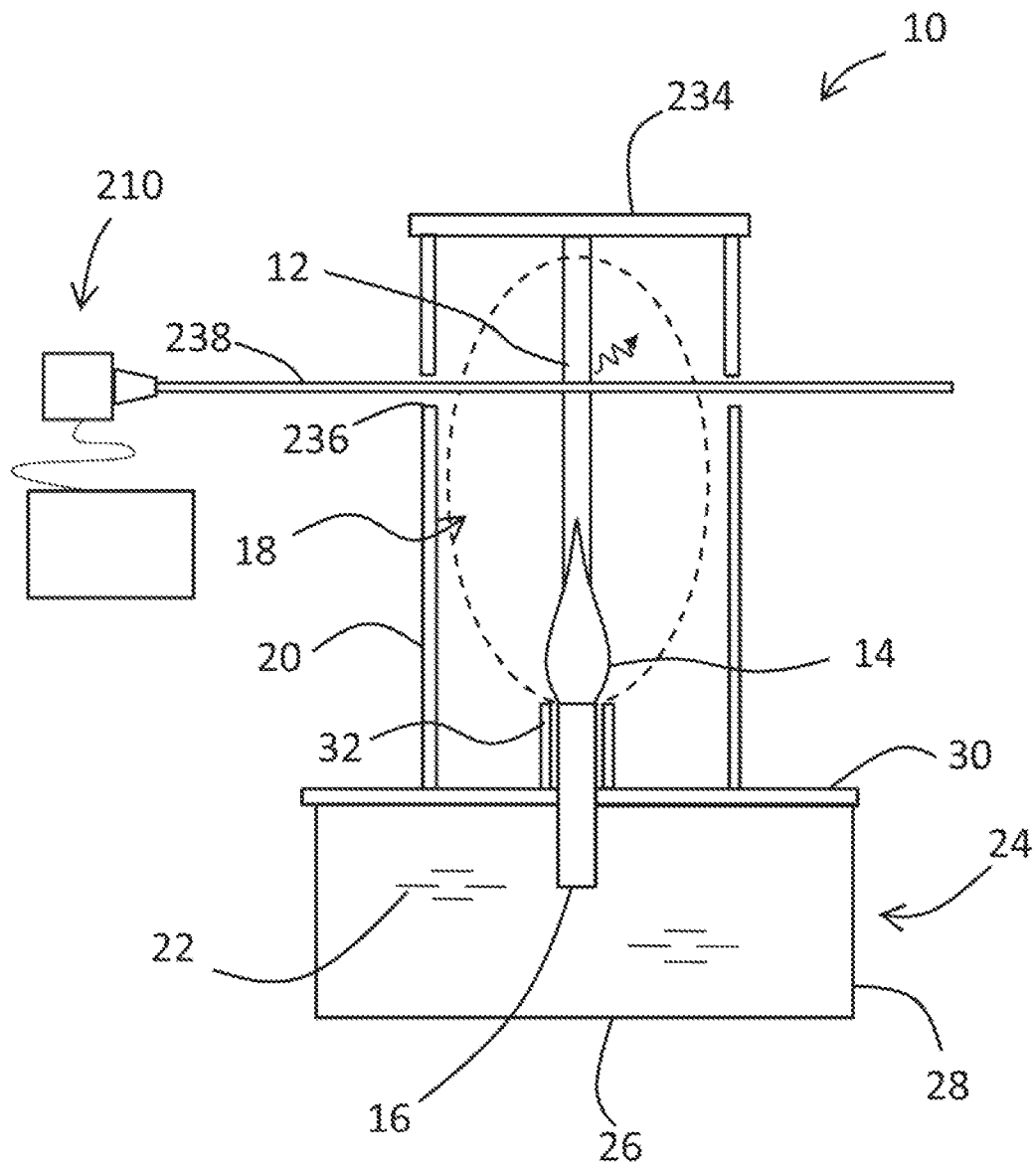
FIG. 2 shows a soot calibration device according to the present invention.

FIG. 2 shows the soot generating apparatus 10 in use as a calibration standard for a soot measuring device 210. The soot measuring device 210 may be any which requires a known quantity of soot production but in the described embodiment is a device which employs a Laser Induced Incandescence, LII, technique. LII is well known in the art and involves the use of short laser pulses to rapidly heat the soot particles to induce incandescence which can be detected using appropriately placed detectors, and the results used to calculate the amount of soot concentration in an exhaust gas.

If a laser beam or laser light sheet much smaller than the soot stream is used in LII, the cross-sectional area of the soot stream can be determined by translating the beam relative to the soot stream and plotting the LII signal intensity as a function of beam position. Alternatively, a horizontal light sheet, perpendicular to soot stream flow direction, could be used, and an image of scattered light, or LII, recorded by a camera viewing the light sheet at a small angle to the flow direction. Dimensions of the cross section of the soot stream could be determined from this image when geometric distortions due to the viewing angle are accounted for.

In FIG. 2, there is shown a modified soot generating apparatus 10 having similar features as denoted by common reference numerals to those described in relation to FIG. 1. However, in the embodiment of FIG. 2, the soot collecting device 34 is not required and is replaced by a suitable exhaust system 234. Also, the gas diffusion shield 20 includes apertures 236 on either side of the soot stream through which laser beam 238 is fired to provide the LII.

A detector (not shown) is used to detect the incandescence of the soot particles and determine the soot per volume concentration within the post-flame zone 18 using known techniques. The comparison of the detected amount to the expected amount produced by the soot generating device can then be used to calibrate the soot measuring apparatus 210.

In most LII systems the detector is placed at right angles to the laser beam direction. However, LII is emitted in all directions and so the detector may be located in other places. The gauze will reduce the amount of light collected, but this can be accounted for by calibration with a known intensity light source, for example, a standard blackbody. Alternatively, a transparent window could be mounted in the gauze to increase the amount of detected LII, though losses due to reflection at the window surfaces would still have to be accounted for.

It will be appreciated that other modifications may be included within the scope of the claimed invention. For example, the gas diffusion shield may extend inwards towards the wick shield to allow a flow of air to entrain into the burning zone from beneath the flame. Also, the gas diffusion shield may not have evenly distributed apertures but may include one or more holes to allow inspection equipment or sensors or the like to enter the burning zone. Further, the gas diffusion shield may not surround the entirety of the burning zone. Portions, for example, the upper portion, may have a solid wall construction, or a reduced flow rate.

Although the description of the calibrated soot measuring device is an LII device, it is envisaged that other measuring devices may be calibrated using the soot generating device of the invention.

The invention claimed is:

1. A soot generating device suitable for calibration purposes, comprising:
   a wick located relative to a burning zone;
   a gas diffusion shield surrounding the burning zone, the gas diffusion shield allowing a continuous stream of air into the combustion zone;
   a fuel supply for delivering fuel to the wick; and,
   a collection device for collecting the soot.

2. A device as claimed in claim 1, wherein the gas diffusion shield is a gauze material.

3. A device as claimed in claim 2, wherein the gauze material includes apertures having a maximum diameter of less than 2.0 mm.

4. A device as claimed in claim 1 wherein the wick is surrounded by a shield.

5. A device as claimed in claim 4, wherein the wick and shield are coterminous relative to a plane defined by the terminal end of the shield.

6. A device as claimed in claim 5, wherein the collection device is a particle filter.

7. A device as claimed in claim 1 wherein the fuel supply includes an aviation, marine, land transport or other prime mover fuel.

8. A method of calibrating a soot generating device comprising: a wick located relative to a burning zone; a gas diffusion shield surrounding the burning zone, the gas diffusion shield allowing a continuous stream of air into the combustion zone; a fuel supply for delivering fuel to the wick; and, a collection device for collecting the soot, the method comprising:
  providing the wick with fuel;
  igniting the fuel so as to provide a flame in the burning zone;
  burning the fuel for a predetermined time; and,
  determining a quantity of soot produced for the predetermined time.

9. A method as claimed in claim 8, further comprising determining the rate of soot production.

10. A method as claimed in claim 9, wherein the quantity of soot is determined by weighing the deposited amount.

11. A method as claimed in claim 8, wherein the quantity of soot is collected in a predetermined time which is in excess of 8 hrs.

12. A method of calibrating a laser using the soot generating apparatus of claim 1, comprising the steps of:
  generating a known stream of soot with the soot generating apparatus;
  using a sensor of a soot measuring apparatus to be calibrated to sense the soot stream or a portion thereof;
  comparing the sensed amount of soot with the known amount of soot to provide a measure of calibration.

13. A method as claimed in claim 12, wherein the soot measuring apparatus uses a laser induced incandescence technique.

* * * * *